United States Patent
McCandless

(10) Patent No.: US 7,321,424 B2
(45) Date of Patent: Jan. 22, 2008

(54) SELF-REFERENCING INSTRUMENT AND METHOD THEREOF FOR MEASURING ELECTROMAGNETIC PROPERTIES

(75) Inventor: James A. McCandless, Lancaster, MA (US)

(73) Assignee: Acton Research Corp., Acton, MA (US)

( * ) Notice: Subject to any disclaimer, the term of this patent is extended or adjusted under 35 U.S.C. 154(b) by 0 days.

(21) Appl. No.: 11/197,195

(22) Filed: Aug. 4, 2005

(65) Prior Publication Data

US 2006/0055932 A1 Mar. 16, 2006

Related U.S. Application Data

(60) Provisional application No. 60/598,935, filed on Aug. 5, 2004.

(51) Int. Cl.
G01J 3/42 (2006.01)
(52) U.S. Cl. ..................................... 356/319
(58) Field of Classification Search ............... None
See application file for complete search history.

(56) References Cited

U.S. PATENT DOCUMENTS

| | | | | |
|---|---|---|---|---|
| 4,210,401 A | * | 7/1980 | Batten | 356/369 |
| 4,266,131 A | * | 5/1981 | Ahjopalo et al. | 250/341.1 |
| 4,578,762 A | | 3/1986 | Wong | 364/497 |
| 4,777,610 A | | 10/1988 | Barwick et al. | 364/563 |
| 2002/0075486 A1 | | 6/2002 | Zhang et al. | 356/630 |

FOREIGN PATENT DOCUMENTS

| | | |
|---|---|---|
| DE | 27 50 421 | 5/1979 |
| DE | 3234534 | 5/1984 |
| EP | 0 290 657 | 11/1988 |
| EP | 0 339 845 | 11/1989 |
| JP | 06049641 | 2/1994 |

OTHER PUBLICATIONS

International Search Report and Written Opinion; Nov. 18, 2005; 14 pages.

* cited by examiner

*Primary Examiner*—Tu T Nguyen
(74) *Attorney, Agent, or Firm*—St. Onge Steward Johnston & Reens LLC

(57) ABSTRACT

In a self-referencing instrument for measuring electromagnetic radiation, a mounting member to which a sample can be coupled moves the sample such that, in a first position, the electromagnetic radiation impinges on the sample, and, in a second position, the electromagnetic radiation does not impinge on the sample. A detection unit receives the electromagnetic radiation from the sample and generates a sample signal when the sample is in the first position, and the detection unit receives the electromagnetic radiation from the source and generates a reference signal when the sample is in the second position. A processor coupled to the detection unit processes the reference signal and the sample signal. This results in a continuous, accurate reference measurement, and permits the instrument to efficiently compensate for error, while offering accurate measurements.

17 Claims, 10 Drawing Sheets

SELF-REFERENCING INSTRUMENT AND METHOD THEREOF FOR MEASURING ELECTROMAGNETIC PROPERTIES

RELATED APPLICATIONS

This application is based on U.S. Provisional Patent Application No. 60/598,935 filed on Aug. 5, 2004.

BACKGROUND OF THE INVENTION

Photometers and spectrophotometer can perform a variety of functions, such as measuring spectral properties of discrete solid, liquid or gas samples, and providing in-situ or on-line continuous measurement and control of manufacturing processes. Photometers generally measure changes in light intensity over time, while spectrophotometers generally measure light levels over a spectrum of colors or wavelengths. These instruments are therefore useful in many applications, including the monitoring and control of industrial processes such as chemical analyses and biological fluid analyses, and in the manufacturing of optical coatings.

Quality photometers require stable and low noise baseline signals over time while quality spectrophotometers require stable, low noise, and linear baseline signals over a spectrum of colors, as well as during the time measurements are being taken. Therefore, conventional photometers and spectrophotometers generally require high-performance components such as very stable and precise power supplies, light sources, detectors, mirrors, moving parts, and electronics. Furthermore, such instruments must be designed to compensate for any residual non-linearities and noise.

Another important requirement is the need to the control or compensate for stray, scattered, or extraneous light that may occur or be present during the measurements. Therefore, conventional instruments must usually be kept in tightly-controlled environments in order to obtain a high degree of stability for extended periods of time. This is required to minimize the noise that mixes with the signal, for example, low frequency noise such as signal drift. Although conventional instruments incorporate high-performance components to minimize such noise, the need for initial, periodic, and even continuous baseline correction remains. Oftentimes, a beam-splitter will be inserted before the sample to create a less than ideal quasi-reference beam.

Process photometers often require a light chopper or a pulsed light source combined with a lock-in amplifier to help provide precise measurements. However, chopper/lock-in add-ons do not eliminate all sources of noise. In fact, light choppers and lock-in amplifiers often add other noises to the signal, while increasing cost and complexity.

Monitoring systems, for example, are often used in the manufacture of coatings. Optical coatings modify the reflectance, absorbance, and transmittance properties of optical components. Due to the interactions of light with extremely thin films of optical materials, it is essential that the thicknesses of the coatings be accurately controlled so that the optical components achieve the desired properties required for the corresponding applications. Conventional monitoring systems measure the growth of thin-film optical coatings by providing in-situ transmittance and/or reflectance measurements of a stationary witness sample while it is being coated along with the nearby moving production substrates. The production parts are usually placed on rotating plates, domes, or planetary fixtures in order to make the coatings substantially uniform in thickness regardless of their location in the supporting structure.

However, the approaches offered by conventional monitoring systems often suffer from several limitations, including the generation of a signal which is contaminated by various sources of noise and the lack of stability of the witness glass. Such noise may originate from process heating and cooling components, mechanical flexing of the chamber, vibrations from on-board equipment such as motors or pumps, emission changes in the light source and noise from the detectors or electronics.

Additional signal problems arise from the coating, creep or deterioration of other optical components in the light path, such as the optical port windows of the coating chamber. Still more noise can originate from intense and highly variable nearby background light sources such as process heaters, thermal sources, and electron beam guns. Conventional optical monitors use a variety of schemes with limited success to combat these problems. These schemes include but are not limited to: use of choppers and lock-in amplifiers to modulate and demodulate or extract most of the signal from the noise, use of beam splitters and reference detectors to monitor the light beam just before it enters the process tank, placement of the monitoring samples and other optics such as to minimize impact from the above process effects, the use of optical fibers, the use of electronic filters to remove as much noise as possible, and digitization of the signals as soon as possible after it emerges from the process vessel.

SUMMARY OF THE INVENTION

In accordance with a first aspect of the invention, there is a provided a self-referencing instrument for measuring properties of electromagnetic radiation. The self-referencing instrument comprises a source of the electromagnetic radiation, a mounting member to which a sample can be coupled, a detection unit, and a processor. The mounting member moves the sample such that, in a first position, the electromagnetic radiation impinges on the sample, and, in a second position, the electromagnetic radiation passes through an opening of the mounting member, such that the electromagnetic radiation does not impinge on the sample. The detection unit receives the electromagnetic radiation and generating signals therefrom. The detection unit receives the electromagnetic radiation from the sample and generates a sample signal when the sample is in the first position, and the detection unit receives the electromagnetic radiation from the source and generates a reference signal when the sample is in the second position. The processor coupled to the detection unit processes the reference signal and the sample signal. The mounting member can move the sample between the first and second positions such that multiple reference signals can be generated to correspond with multiple sample signals.

In accordance with certain embodiments, the mounting member is rotatable, wherein the sample and the opening are rotated into the beam of electromagnetic radiation. In accordance with other certain embodiments, the mounting member articulates the sample and the opening into the beam of electromagnetic radiation.

In accordance with certain embodiments, apertures for the sample and the opening are substantially the same.

In accordance with certain embodiments, the sample provides a minimum of deflection, scatter, displacement, divergence, convergence, and distortion to the impinging beam of electromagnetic radiation.

In accordance with certain embodiments, when the sample is in a third position, the electromagnetic radiation is substantially blocked from the detection unit.

In accordance with certain embodiments, the instrument is a photometer. In accordance with other certain embodiments, the instrument is a spectrophotometer.

In accordance with certain embodiments, when the sample is in the first position, the electromagnetic radiation received by the detection unit is transmitted through the sample. In accordance with certain embodiments, when the sample is in the first position, the electromagnetic radiation received by the detection unit is reflected from the sample.

In accordance with certain embodiments, the mounting member is a substantially circular plate, while in other embodiments, the mounting member is a shaft movable along an axis, the sample being coupled to the shaft.

In accordance with certain embodiments, the processor computes losses from the processed sample signal and reference signal.

In accordance with certain embodiments, a speed of movement of the mounting member is optimized for measuring the properties of the electromagnetic radiation. In accordance with certain embodiments, the system may further comprise a mask that is adjacent to the mounting member. When the mounting member comprises a plurality of openings and a corresponding plurality of sample regions, the mask exposes a single opening and a corresponding single sample to the radiation while covering other openings and corresponding sample regions. The driver is coupled to the mounting member by a first shaft. In one embodiment, the mask is rotatable with respect to the mounting member via a second shaft coupled to the mask. The first and second shafts are coaxial.

In accordance with certain embodiments, the processor may process the reference signal and the sample signal to determine a thickness of a coating being applied to the sample and components, and the processor may process spectral features of a coating being applied to the sample.

In accordance with another aspect of the invention, there is provided a spectrophotometer comprising a mounting member, a driver, a source, a detection unit, and a processor. The mounting member includes at least one opening and at least one sample region at which a sample can be coupled to the mounting member. The driver is coupled to the mounting member for moving the mounting member. The directed source generates electromagnetic radiation. The radiation passes through the at least one opening to create a first reference signal when the mounting member is in a first position, and the radiation passes through the at least one sample to create a first sample signal when the mounting member is in a second position. The detection unit receives the first reference signal and the first sample signal. The processor is coupled to the detection unit for processing the first reference signal and the first sample signal.

In accordance with certain embodiments, the detection unit detects a reflected second sample signal from the sample, wherein the processor processes the second sample signal.

In accordance with certain embodiments of the present invention, the mounting member of the system may further comprise a reflector region to which a reflector can be coupled. The at least one opening, the at least one sample region, and the reflector region can be substantially equidistant from a rotational center of the mounting member. The radiation impinges on the reflector to generate a reflected second reference signal when the mounting member is in a third position. In this manner, the processor processes the first and second sample signals and the first and second reference signals to determine a thickness of a coating being applied to the sample, and components. In addition, the processor coupled to the detection unit can process the reflected second sample signal and the second reference signal to determine a thickness of a coating being applied to the sample.

In one embodiment, the mounting member is a substantially circular plate. The at least one sample region and the at least one opening are substantially equidistant from a rotational center of the mounting member. In another embodiment, the mounting member is a shaft along an axis, wherein the at least one opening and at least one sample region are positioned on the shaft.

The driver is preferably a motor, and is preferably coupled to the mounting member by a shaft.

In accordance with certain embodiments, when the mounting member is in a fourth position, the electromagnetic radiation is substantially blocked from the detection unit.

In accordance with certain embodiments, apertures for the at least one sample and the at least one opening are substantially the same. In accordance with another aspect of the present invention, there is provided a spectrophotometer system comprising a mounting member, a driver, a directed source, a detection unit, and a processor. The mounting member includes at least one opening and at least one sample cell. The at least one sample cell receives a process solution. The at least one opening and at least one sample cell are coupled to the mounting member. The driver is attached to the mounting member for moving the mounting member. The directed source generates electromagnetic radiation. The radiation passes through the at least one opening when the mounting member is in a first position. The radiation passes through the process solution in the at least one sample cell to create a sample signal when the mounting member is in a second position. The detection unit receives the reference signal and the sample signal. The processor is coupled to the detection unit, and processes the reference signal and the sample signal.

The spectrophotometer may further comprise a monochromator for selecting a wavelength of electromagnetic radiation. The monochromator is controlled by the processor. The wavelength is selected by at least one of a source selection filter, an optical filter, an optical filter wheel, a prism, and a grating.

In accordance with certain embodiments, when the mounting member is in a third position, the electromagnetic radiation is substantially blocked from the detection unit.

In accordance with certain embodiments, apertures for the at least one sample cell and the at least one opening are substantially the same.

A feature of the present invention is that a reference signal is created at the same location as, and at approximately the same time as, the sample signal. This feature permits accurate measurements, such as transmittance and reflectance measurements to be determined that continuously compensate for common sources of error, such as undesirable optical noise, electrical noise, and low-frequency noise, such as signal drift. This feature of providing continuous, real-time reference signals is advantageous over conventional systems in that the present invention is insensitive to such sources of error, because the reference signal of the present invention compensates for sources of error, such as signal drift, since it "sees" the same noise as well as signal in exactly the same location as the sample. It is also important to note that the reference signal is recorded by the processor just before and just after the sample signal is recorded. In contrast, conventional instruments are sensitive to such sources of noise, and errors resulting from such noise become an adverse factor during a measurement operation. Conventional instruments must therefore introduce additional components and complexity that reduce such noise but they can not compensate for the noise as well as this invention.

In addition, conventional instruments take baseline or reference scans at different times. However, the conventional high-performance components described above may not result in a consistently accurate reference signal due to the resulting time delay between reference measurements, which can cause additional error and thus adversely degrade the performance of conventional systems. Another approach offered by conventional instruments is to use beam-splitters and mirrors to provide a semblance of real time reference measurements. However, this approach creates additional sources of error, further justifying the need for additional high-performance components, and adding cost and complexity. Since the present invention introduces a self-referencing instrument that continuously compensates for the most serious sources of error, such as drift, there is no need to introduce these additional components to the present invention.

Another feature of the present invention is that by adjusting certain parameters of the mounting member, such as its rotational speed, one can control how frequently the reference signal is re-measured. To compensate for higher rates in signal variability, e.g, faster drift, one can increase the wheel speed and re-normalize the sample signal more often. However, there are trade-offs. Higher sampling rates may result in less accurate individual signal measurements because the signal level could decrease and the processor would have less time to process data. However, higher rotation rates will result in more repeat measurements which can be averaged. Also, as the rotation rate increases, the processing electronics and the detector have the processing power to adapt with the higher rate of data collection.

Another feature of the present invention is that a plurality of substrates can be simultaneously measured with new reference measurements being obtained for each set of sample measurements before indexing the self-referencing instrument to the next wavelength. This feature is beneficial, for example, in a spectrophotometer where there is generally a requirement to measure many samples over the same ranges of wavelengths and signal levels. The present invention permits multiple scans to be taken simultaneously, by introducing a mounting member that supports a plurality of samples, wherein each sample signal is created at the same location, and at approximately the same time as, a corresponding reference signal by a beam of electromagnetic radiation. An accurate reference signal is therefore created for each scan. In this manner, a highly accurate, efficient means for spectral scans of many samples can be achieved.

Another feature of the present invention is that transmittance and reflectance measurements can be simultaneously generated over a given spectrum. The present invention achieves this by using the same beam and the same beam handling optics to create the reference and sample signals during a given scan. The sample signal can include transmittance signals and/or reflectance signals, used in the quasi-simultaneous calculations of transmittance and reflectance measurements, respectively. This feature is advantageous over conventional systems, which use spatially separate reference beams to generate reference measurements at different times, thereby preventing conventional systems from processing highly accurate simultaneous transmittance and reflectance measurements.

Another feature is that the present invention can be used to periodically or selectively move the sample in and out of position. This is particularly useful in applications where a rotating member is not advantageous. The coating of some samples in the mounting member is prevented in a coating monitoring application, i.e., a portion of the mounting member would be masked while one hole and one sample are alternately indexed, or articulated, into the beam of the monitoring radiation. This feature is beneficial in several applications, such as in coating monitoring, where it would be advantageous to hold one or more uncoated samples in reserve. This feature also permits the insertion of a new or different sample or substrate into position because the old substrate becomes full, saturated, or too opaque for continued monitoring or because it is desired to "look" at a different property of the process stream or to look at the process stream at a different time.

Another feature is that the self-referencing instrument of the present invention can immediately produce quality data as soon as the various components of the instrument are activated upon initialization. That is, the self-referencing instrument may be turned on, and may operate, without the need for background scans, calibrations, or zeroing.

BRIEF DESCRIPTION OF THE DRAWINGS

The foregoing and other objects, features, and advantages of the invention will be apparent from the more particular description of preferred aspects of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS OF THE INVENTION

Figure 1A:
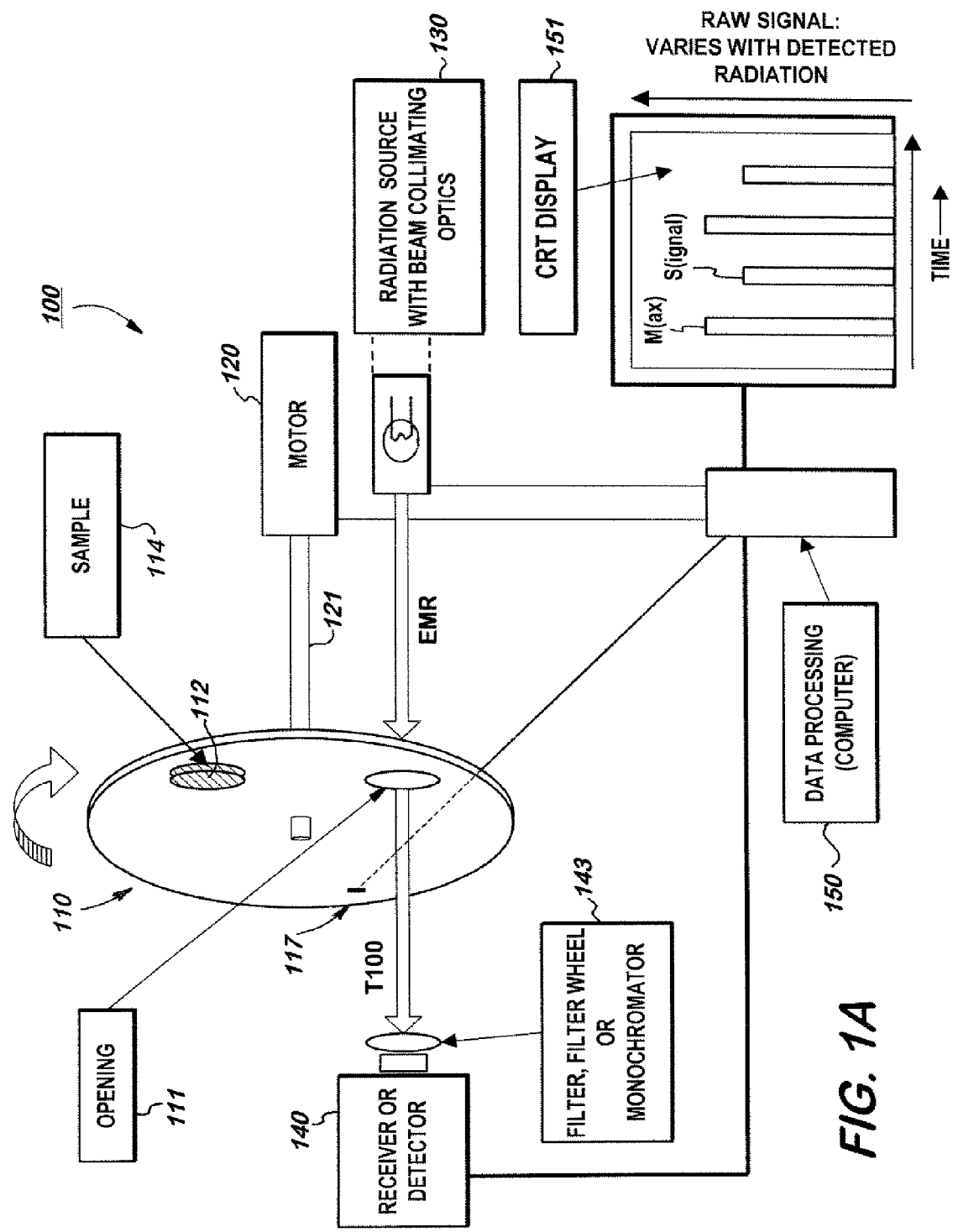
FIG. 1A contains a schematic block diagram illustrating a self-referencing instrument in a first position for measuring a reference transmittance signal according to an embodiment of the present invention.

To address the above limitations of the prior art, a feature of the present invention provides a self-referencing instrument and method for improving the accuracy and speed of spectral measurements while reducing the cost and complexity over conventional photometers and spectrophotometers. The self-referencing instrument of the present invention has the capability to move a sample into and out of a beam of electromagnetic radiation. When the sample is in the beam, the beam impinges on the sample, and sample transmission and reflection measurements may be taken. When the sample is out of the beam, reference transmission and reflection measurements can be taken. Thus, according to the invention, reference signals can be updated frequently, and, in one embodiment, can be updated for every measurement of the sample signals. During a scan operation, for example, during a scan of a given wavelength, an opening can be positioned in front of the beam of electromagnetic radiation such that the electromagnetic radiation passes through the opening and is detected by a detector to create a reference signal. This results in a repetitive and highly accurate real-time reference signal generated via the opening or openings. At approximately the same time that the reference signal is generated, a sample signal is also generated. The sample is rotated or articulated into the beam of electromagnetic radiation. In this manner, the sample can be positioned in front of the beam such that the electromagnetic radiation impinges on the sample, and the reflected and/or transmitted radiation from the sample can be detected to generate one or more sample signals.

The electromagnetic radiation is preferably generated from a source having beam collimating optics. The beam of electromagnetic radiation comprises coaxial signal and reference beams that generate the reference signal and sample signal. A position sensor assembly on the mounting member can generate position signals to a processor to distinguish the sample signal from the reference signal. The position sensor assembly may be a prior art triggering device such as a photocell and slit at the perimeter of the mounting member. A processor processes the reference signal and the sample signal to determine a calculated sample signal, referred to as a final signal, that compensates for any errors that may be introduced due to such factors as room lighting or low-frequency noise, i.e., signal drift. This feature may apply to any relevant measurements, including measurements processed from the signals created by the electromagnetic radiation, for example, the transmittance signal and/or reflectance signal. Since a reference signal can created with a corresponding sample signal for each respective scan, wherein each signal is taken at precisely the same location relative to the electromagnetic radiation, and at approximately the same time, the self-referencing instrument of the present invention can compensate for such noise because the reference signal "sees" the same signal drift as the sample signal, wherein the final transmittance signal and/or final reflectance signal can accurately compensate for the signal drift. It is important to feature that the reference signal and the corresponding sample signal are processed at approximately the same time. The time interval, while negligible for purposes of the present invention, may be nevertheless dependent on various factors, such as processor speed and performance. Since the self-referencing instrument provides for a continuous, accurate reference measurement, and thereby efficiently compensating for error in this manner, the present invention eliminates the need for expensive components that are traditionally used to minimize such noise. In addition, the present invention offers accurate spectral measurements to be attained across a robust spectrum.

Figure 1B:
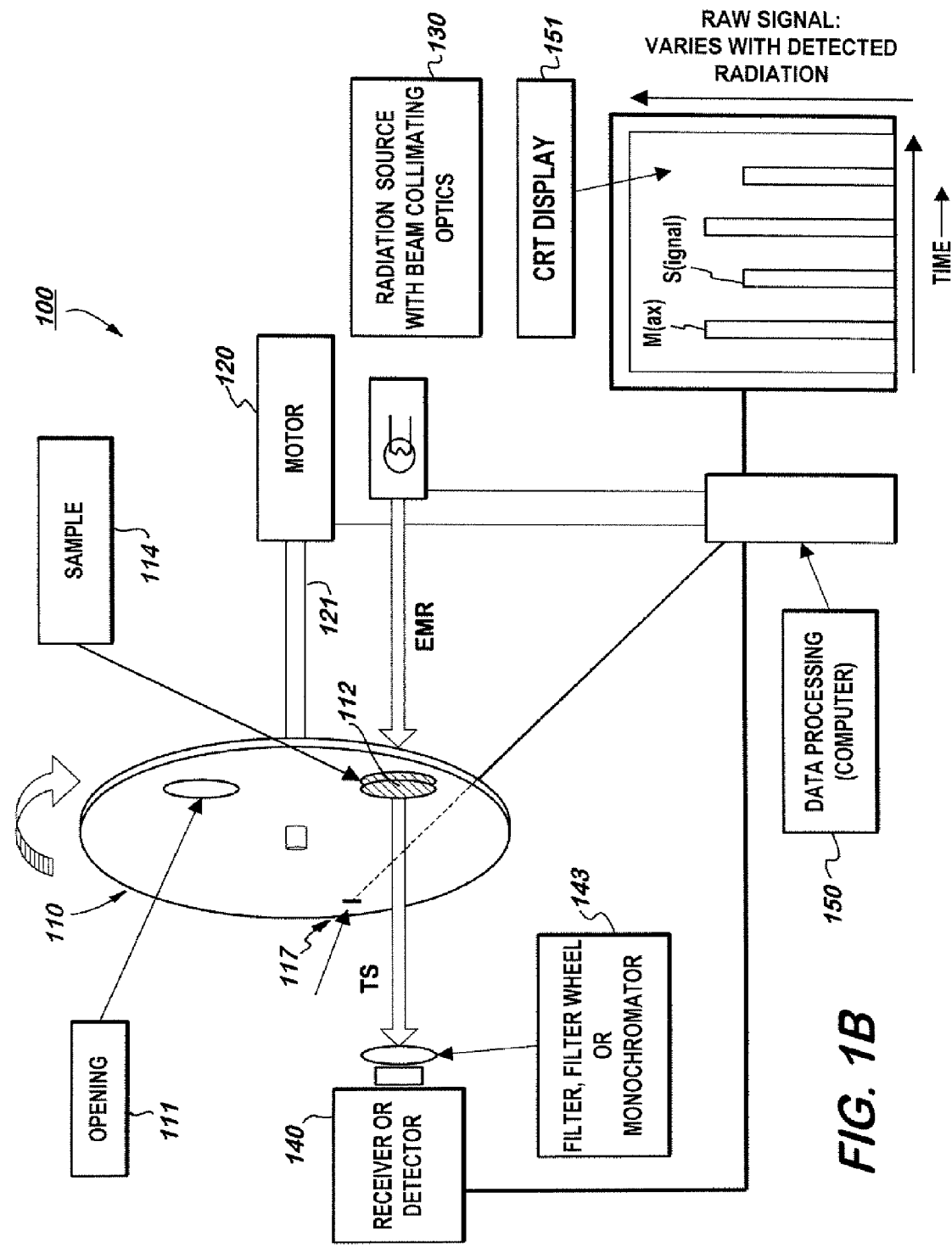
FIG. 1B contains a schematic block diagram illustrating the self-referencing instrument of FIG. 1A in a second position for measuring a sample transmittance signal.

FIGS. 1A and 1B contain schematic block diagrams illustrating a monitoring system 100 according to an embodiment of the present invention. As shown in FIGS. 1A and 1B, in one embodiment, the system 100 includes a mounting member 110, which can be a substantially circular opaque plate or a shaft, a driver 120, which can be a motor, a source of electromagnetic radiation 130, such as light, a detector and signal amplifier or a detection unit 140, and a data acquisition and processing apparatus, for example, a computer 150 connected to a display 151. In addition, the computer is connected to other components of the system, including the motor 120, the source 130, and detection unit 140. The display 151 can be a processed data output device, for example, a TV screen display that presents raw signal data.

In accordance with the invention, in the monitoring system 100 of FIGS. 1A and 1B, the plate 110 comprises at least one opening 111 or aperture, and at least one sample region 112. A sample or substrate 114 at the sample region 112 may be coupled to the plate 110. The sample region 112 may include a hole or aperture onto which the sample 114 can be inserted, or the sample 114 can be coupled to the surface of the plate 110. The apertures for the sample 114 and the opening 111 are substantially the same from the perspective of the impinging beam of electromagnetic radiation, or have geometrically identical or similar clear apertures with respect to the effects to the impinging beam of electromagnetic radiation. The opening 111 and the sample region 112 are substantially equidistant from the rotational center of the plate 110. The plate 110 may be sufficiently opaque to prevent a beam of electromagnetic radiation from passing through the surface of the plate 110.

The openings are located at the same distance from the center of rotation. At least one opening is open, or empty, and at least one other opening serves as a sample region that contains a substrate or sample, such as a glass which collects the coating material. The plate is, except for the apertures, opaque to a continuously monitored beam of electromagnetic energy EME. Any wavelength of radiation, including X-rays and microwaves, can be used in conjunction with the present invention.

As mentioned above, at least one aperture contains a sample or substrate which is mostly transparent to the transmitted electromagnetic energy. The substrate may be a polished witness piece or a production part or both. As the substrate becomes coated with a condensing material which, for example, is evaporated from a source in a vacuum chamber, the amount of electromagnetic energy transmitted through the substrate is increased or decreased, or it oscillates depending on parameters such as the index of refraction of the materials, the thickness of the condensing material, and in accordance with the laws of electromagnetic radiation.

In one embodiment, the opening 111 is located about 190 to 200 or 160 to 170 angular degrees from the sample region 112. These angles are selected to avoid confusion about which signal is the reference signal and which is a raw signal, the raw signal being defined as the light passing through the sample 114. In addition, these angles allow a signal collecting and processing apparatus and program, such as the computer 150, the maximum amount of data collection and processing time before the next data set must be collected and processed. The display 151 can present an output of the raw signal varying with detected radiation over time.

The position sensor assembly 117 provides position signals to the signal collecting and processing apparatus and program 150 which pertain to the rotational position of the mounting member 110, whereby the signal collecting and processing apparatus and program 150 processes the position signals with the digital data. The position sensor 117 is preferably located along the periphery of the mounting member in order to more precisely tell the processor the position of the plate at every revolution. The position sensor allows the processor to distinguish between sample signals and reference signals. The position sensor assembly 117 may be a prior art triggering device such as a photocell and slit at the perimeter of the mounting member, and the position sensor assembly 117 can be a magnetic or optical position sensor assembly. It is preferable that the position sensor assembly 117 be adjustable with respect to wheel position. The position sensor 117 can be adjustable with respect to the plate for synchronization and optimization of the data collection with the data transmission. Furthermore, the position sensor can receive additional data, such as the rate of rotation of the mounting member, and provide additional signals, respectively, to the computer 150.

In FIG. 1A, the reference transmittance signal T100 is created by the beam passing through the opening 111. The beam passing through the opening 111 is unaffected by the coating material because there is no sample or substrate to collect the material, and, therefore, the opening 111 always "sees" 100% of the light. That is, the opening 111 may be an empty hole that blocks none of the radiation when in the path of the radiation, and thus generating a 100% maximum signal. The empty hole or opening 111 thus serves as a way to continuously monitor the beam, i.e., virgin photon beam, and even to correct for most of the system noise and false signals which can adversely degrade the performance of other similar coating monitoring systems.

In addition, the opaque portions of the plate 110 serve to clearly separate the signal, the lack of signal, i.e., 0% transmission, and the reference signal, i.e., 100% transmission. In one particular embodiment in which the invention is applied to a coating system, as described below in detail, there are methods of minimizing the adverse effects of coating material that passes through the opening 111. However, a key advantage of the present invention is that the transmittance signal T, which may be calculated by the equation $T=Ts/T100$, as described below, automatically compensates for any stray coating on other optical surfaces in a coating plant, for example, on entrance and exit windows, or beam controlling mirrors or lenses. This is because the sample transmittance signal Ts and the reference transmittance signal T100 "see" about the same effects from this stray coating. Further, in one embodiment, a tube can be coupled around the opening 111 to minimize any undesirable coating material that may pass through the opening 111 and deposit on the back of the sample 114. Details regarding the transmittance signals T, T100, and Ts are described below. Further, the sample 114 may be polished on both sides, such that both sides of the sample 114 are substantially parallel and flat. The sample is constructed so as to offer a minimum of deflection, scatter, displacement, divergence, convergence or distortion to the impinging beam of electromagnetic radiation.

The motor 120 rotates the plate 110 via a shaft 121 that is coupled to the motor 120 and to the center of the plate 110 for rotating the plate 110. In this manner, the plate 110 can be rotated by the motor 120 at virtually any speed, and, in one particular embodiment, at speeds ranging at least from 5 to 500 RPM. The selected rate of rotation depends on factors such as practical sample rotation speed constraints, the distance of a monitoring spot, i.e., the position where a beam of electromagnetic radiation intersects the mounting member, from the center of rotation of the plate 110, the size, or optical arc-length of the mounting sample, and the desired sample collection rate versus data precision. Another factor is the number of wavelengths required to be monitored during a monitoring process, since, in one embodiment, measurements are taken at one wavelength per rotation. That is, the spectral scan rate is directly proportional to the rotation speed. In another embodiment, the data signal level is inversely proportional to the rotation speed. Rotation rate is generally not a critical parameter but it does usually have an optimal value for each application. As an alternative to continuous rotation of the plate 110, the plate 110 may be controlled to articulate to the various required data collection positions.

The source 130 generates a continuous beam of electromagnetic radiation at the plate 110. The source 130 can comprise beam collimating optics to produce a directed beam of electromagnetic radiation at approximately the same size, or smaller than, the opening 111. The source 130 can be one or two directed sources of electromagnetic radiation, for example, a source of optical radiation, such as a light source, focusing, directing, and collecting gimbals, apertures, polarizers, and refractive and/or reflective optics.

One or two beams of electromagnetic radiation, for example, optical radiation such as light, are continuously impinged on the plate at the aperture radii. As described below, the transmitted/reflected beams are collected via a suitable detector and processed, resulting in a highly accurate and noise insensitive signal. In addition, as described below, there are several distinct components to the resulting signal that are processed by a processor for use in determining optical properties such as a coating thickness of a coating being applied to the sample.

In FIGS. 1A and 1B, during each rotation of the plate 110, the light beam passes through the opening 111 and the sample 114 in the sample region 112. The detection unit 140 may receive transmittance signals of the light beam from the opening 111 and the sample 114. In addition, a filtering unit may select a desired frequency of radiation. In this manner, a filter, filter wheel, or monochromator 143 may intercept the transmittance signals of the light beam from the opening 111 and the sample 114. In addition, the detection unit 140 may receive sample reflectance signals of the beam that are reflected from the sample 114. In addition, as described above, the detection unit 140 may generate the dark signal Td. The dark signal is the optical zero reference and is important for making low light level measurements such as in the blocking spectral region of optical filters. The dark signal Td may be generated whenever the opaque plate 110 blocks the light beam from the detection unit 140. For example, during rotation of the plate 110, the light beam may impinge upon the plate 110 while the detection unit 140 generates a detection signal, which serves as the dark signal Td. The dark signal Td may be approximately zero when the plate 110 is an opaque plate.

The data acquisition and processing apparatus 150 is coupled to the detection unit 140 for processing the transmittance signals of the beam from the opening 111 and the sample 114. The data acquisition and processing apparatus 150 comprises an analog-to-digital converter (ADC) (not shown) which converts the received transmittance signals into digital data, which are then processed by the data acquisition and processing apparatus 150. The data acquisition and processing apparatus 150 may be a computer, and may further include a data and control interface card (not shown). In this manner, the computer 150 may provide additional functions such as process control, data collection, data processing display, and interface programs. The computer 150 may receive, identify, and process the received digital data from the analog-to-digital converter, as well as the position sensor 117, and generate and display data and graphics to a display unit. The computer 150 generates a calculated transmittance signal, and/or a calculated reflectance signal, from the received digital data, and displays data and graphics via the display 151, pertaining to the calculated transmittance signal in relation to time. In addition, the computer 150 can calculate losses from the transmittance signal and the reflectance signal. For example, absorbance calculations may be generated.

As with any practical spectrophotometer, the present invention includes means for collecting and processing the data. Except for specialized programming, and the apertured filter holding member, all of the necessary peripherals to accomplish these tasks are commercially available from companies such as Acton Research Corp., Spectra-Physics/ Oriel, Keithley Instruments, Dell, Apple and other desktop or rack-mounted computer vendors.

In order to use the invention at different wavelengths, one or more approaches may be employed. One approach is to switch different monochromatic light sources on and off or to physically move the different light sources into the light source position, for example, light source position 130. Another approach is to use a broad-spectrum light source such as a tungsten or Xenon source and select wavelengths from this source by using either band-pass filters or a monochromator. The monochromator can be manually or automatically adjusted to select the desired wavelength or wavelengths in combination with an appropriate detector or detector array. An advantage of a detector array such as a charged coupled detector CCD array is that the spectral scanning can be made very fast, and only limited by the response times of the detectors, signal amplification electronics, data and control interface card, and computer. The data and control interface card (not shown), for example, accurately collects the raw detector data in the form of analog signals, digitizes the analog signals, and stores the digitized signals so that the computer, in concert with the process control programs, can catalog, process, and display the results for a system operator.

A spectrophotometer software application generally has several components and is written to perform several functions. The software application controls associated hardware in a manner whereby the system produces optimal results for the user. Typical system components perform control functions such as controlling the motor and its shaft position and rotation speed, monitoring the position sensor 117 for triggering data collection and storage into the correct data areas, turning on and off, changing intensity and position of, or otherwise selecting a light source; controlling the order sorting filters, slit width, and wavelength or wavelengths, or selecting the grating of the monochromator, turning on and off, and adjusting, the electronic filtering and gain of the detectors; accessing and controlling the data card and its data stream; and controlling standard computer peripherals such as the hard drive, monitor, network card, and printer.

The data processing software takes advantage of the repetitive and highly accurate real-time reference signals supplied by virtue of the opening or openings in the rotating or articulating plate, in accordance with the present invention. Conventional spectrometers also take advantage of reference signals, but such conventional reference scans or reference points are taken at different times or are gathered much more slowly than the reference signals of the present invention. This is important since signal drift between baseline reference corrections must be eliminated and/or corrected in order to produce a quality instrument. Other important quality determinative features of spectrometers to be considered include wavelength resolution, wavelength accuracy, signal accuracy, and signal-to-noise ratio.

Referring to FIG. 1A, the plate 110 of the monitoring system 100 is in a first rotational position, in which the detection unit 140 receives the beam that has passed through the opening 111 to create a reference transmittance signal T100. The first position may be established during a rotation of the plate 110, or by articulating the opening 111 into the beam. During an operation in which, for example, a coating is being applied to workpieces such as lenses, as well as the monitored sample 114, the beam passing through the opening 111 is unaffected by coating material that would have accumulated on the sample 114. As a result, approximately 100% of the beam passes through the opening.

The present invention creates a true reference transmittance signal T100. This feature therefore offers several advantages over conventional systems. In particular, the reference transmittance signal T100 serves as a way to correct the beam for undesirable optical and/or electrical noise that may be generated by various components or from stray light.

In FIG. 1B, the plate 110 of the monitoring system 100 is in a second position, in which the detection unit 140 receives the beam that has passed through the sample 114 of the sample region 112 to create a sample transmittance signal Ts. The second position may be established during a rotation of the plate 110, or by articulating the sample 114 into the beam. The data acquisition and processing apparatus 150 converts the sample transmittance signal Ts into digital data, which is processed by the data acquisition and processing apparatus 150.

The detection unit 140 creates the reference transmittance signal T100 based on the beam received after passing through the opening 111, and the detection unit 140 creates the sample transmittance signal Ts based on the beam received after passing through the sample. The sample 114 therefore blocks some radiation when in the path of the beam, and thus generates the sample signal. The detection unit 140 can also create a dark signal Td, which is nearly zero, whenever the beam is blocked from the detection unit 140 by the opaque plate 110. In addition, the invention also operates-without the dark signal Td since this would usually be residual electronic noise and may be insignificantly small. The dark signal Td may be required in cases were Ts is small, for example, where Ts is less than 20 times Td.

The data acquisition and processing apparatus 150 generates the calculated final transmitted signal T from the received reference transmittance signal T100, sample transmittance signal Ts, and dark signal Td. The transmitted signal T may be used, for example, to monitor and control optical properties such as the thickness of a coating on an optical component.

For a normal angle of incidence, the processor generates the final transmitted signal T based on the following equation (1):

$$T = [(Ts - Td)/(T100 - Td)] \quad (1)$$

In the equation (1) above, the final transmitted signal T is calculated based on a normal angle of incidence. However, for non-normal incidence cases, variations on equation (1) are applied. Such variations would be readily known to those skilled in the art of the invention. For large angles of incidence, above about 20 degrees, in order to obtain accurate results, it may be necessary to insert a polarizer in the beam path just before the beam enters the sample chamber. Also, calculations for the non-normal-incidence case can be generated from other standard equations or by using commercial software packages, for example, software packages developed and sold by optical thin film design and signal analysis specialists.

Figure 2:
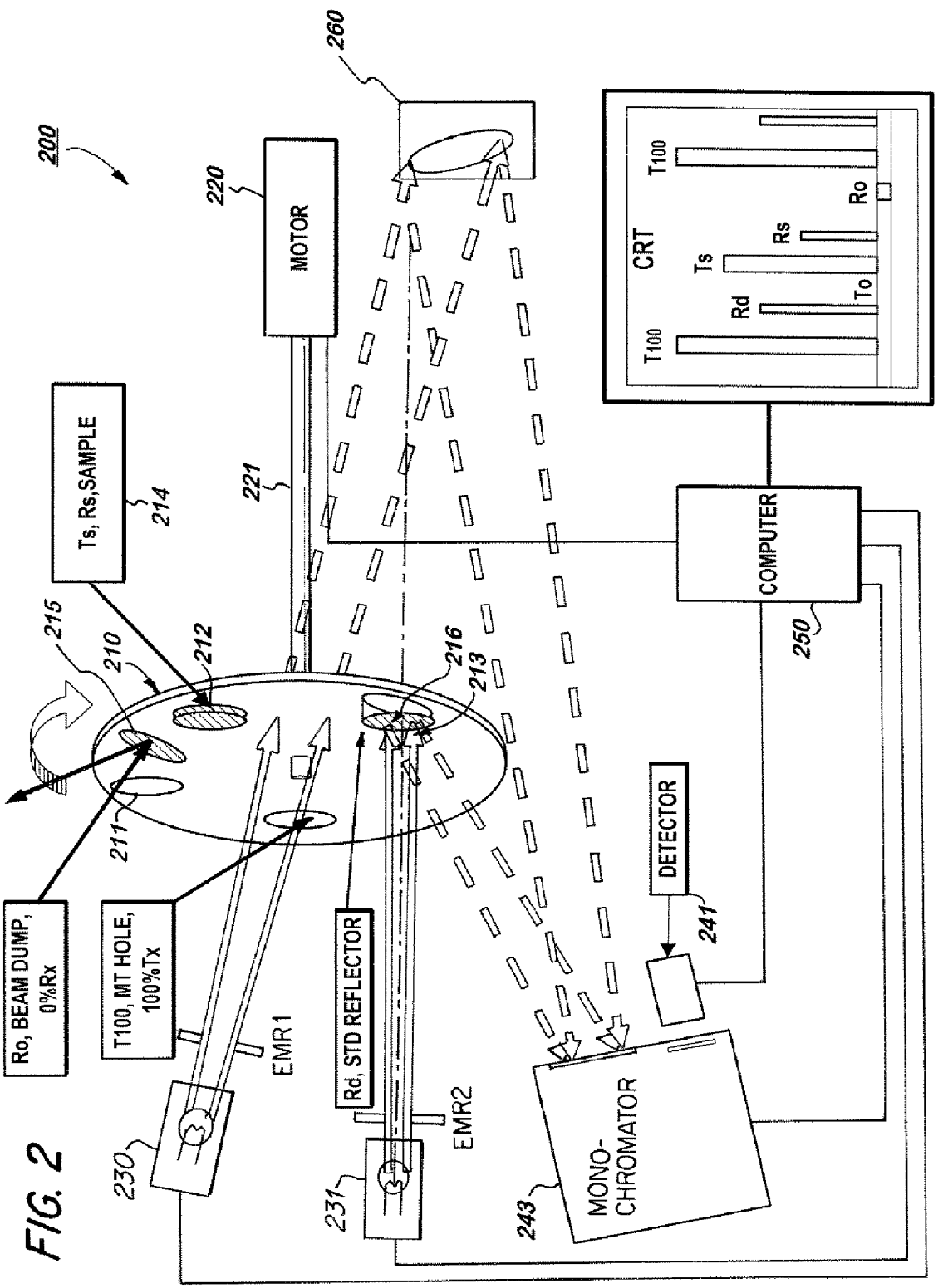
FIG. 2 contains a schematic block diagram illustrating a self-referencing instrument illustrating the near-simultaneous measurement of the reflectance and transmittance of a sample.
Figure 3:
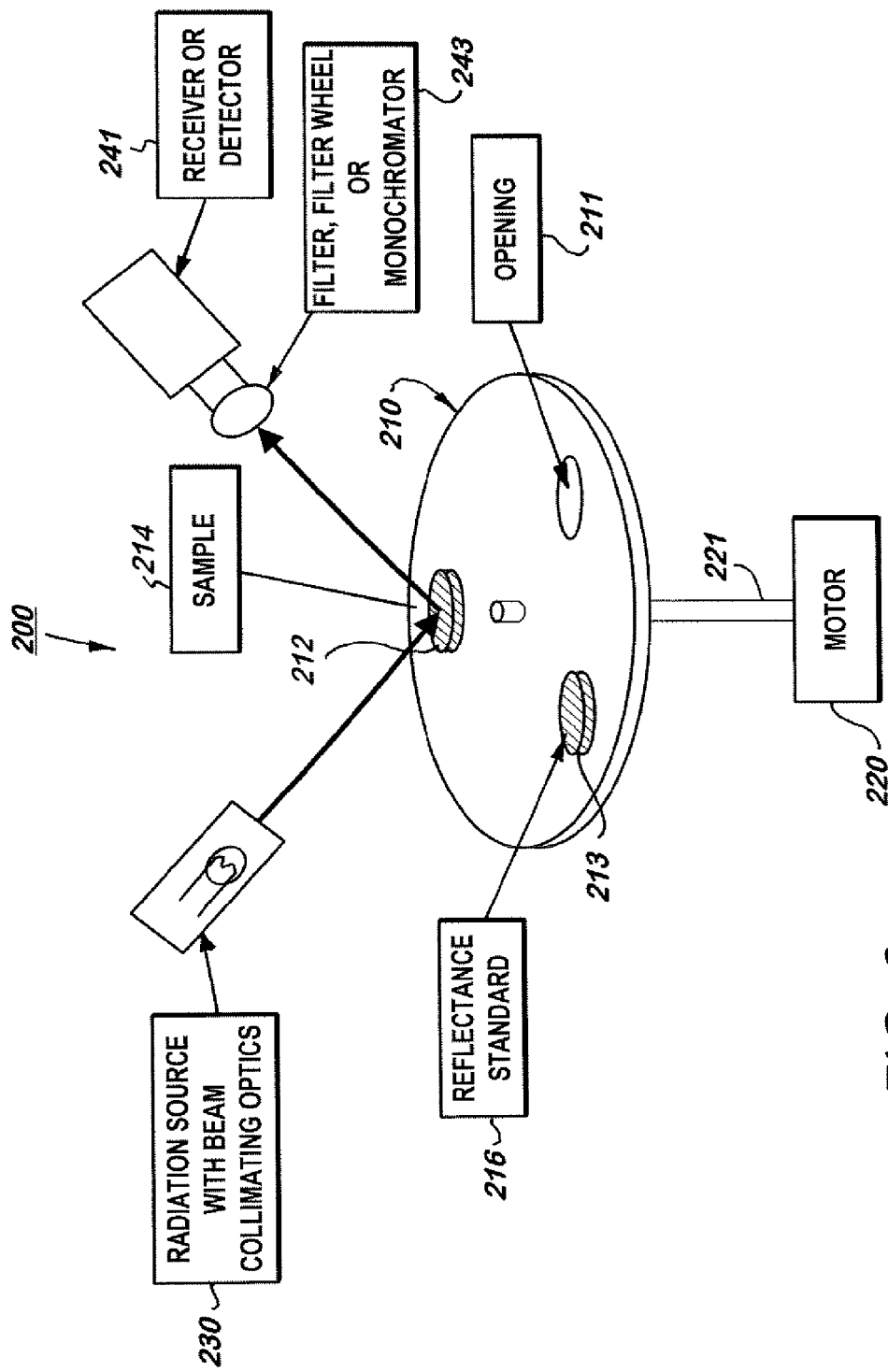
FIG. 3 contains a schematic block diagram illustrating the self-referencing instrument of FIG. 2 for measuring reflectance signals.

FIGS. 2 and 3 contain schematic block diagrams illustrating another embodiment of the monitoring system 200 of the invention. In the embodiment of FIGS. 2 and 3, reflectance measurements are used in addition to the transmittance measurements used in the embodiment of FIGS. 1A and 1B. As shown in FIG. 2, the system 200 comprises a mounting member 210, such as a substantially circular opaque plate or a shaft, a driver 220, such as a motor, two sources of directed, collimated or high F/# electromagnetic radiation 230, 231, which can be light sources combined with lenses, mirrors and or apertures, a reflective device 260, such as a mirror or grating, a first detection unit 241, a monochromator 243, a data acquisition and processing apparatus, for example, a computer 250 connected to a display 251. In addition, the computer 250 is connected to other components of the system, including the motor 220, the sources 230, 231 and detection unit 241. The display 251 can be a processed data output device, for example, a TV screen display that presents raw signal data. The plate 210 comprises at least one opening 211 and at least one sample region 212. A sample 214 at the sample region 212 may be coupled to the plate 210. The sample region 212 may include a hole into which the sample 214 can be inserted, or the sample 114 can be coupled to the surface of the plate 210. The opening 211 and sample region 212 are substantially equidistant from the rotational center of the plate 210. The plate 210 may be sufficiently opaque to prevent a beam or beams of electromagnetic radiation from passing through the surface of the plate 210.

Further, the sample 214 may be polished on both sides, such that both sides of the sample 214 are substantially parallel and flat. The sample is constructed so as to offer a minimum of deflection, scatter, displacement, divergence, convergence or distortion to the impinging beam of electromagnetic radiation.

In one embodiment, the plate 210 also comprises a reflector region 213. The reflector region 213 preferably includes a reflectance standard 216 that generates a reference signal, and is composed of a material having high reflectance properties, for example, a highly polished wedge of polycrystalline. The reflector region 213, the opening 211 and the sample region 212 are substantially equidistant from the center of the plate 210.

The motor 220 rotates the plate 210 via a shaft 221 that is coupled to the motor 220 and to the center of the plate 210 for rotating the plate 210. In this manner, the plate 210 can be rotated by the motor 220 at virtually any speed, and, in one particular embodiment, at speeds ranging from 5 to 500 RPM. In another embodiment, the mounting member 210 is a shaft along an axis, whereby the motor 220 is coupled to shaft by a driver shaft.

The sources 230, 231 generate continuous beams of electromagnetic radiation EMR1, EMR2 directed toward the plate 210. The sources 230, 231 can be one or two directed sources of electromagnetic radiation, for example, a source of optical radiation, such as a light source. During operation, a continuous beam is directed at a monitoring spot, i.e., a position where the beam intersects the plate 210. For example, when the plate 210 is in a first position of rotation, whereby the opening 211 is at the monitoring spot, the beam passes through the opening 211 at the monitoring spot to create the reference transmittance signal T100.

In FIG. 3, the plate 210 is in a second position of rotation, whereby the sample 214 is at the monitoring spot, and the beam passes through and reflects from the sample 214 in the sample region 212 at the monitoring spot to create the sample transmittance signal Ts and a sample reflectance signal Rs. The A portion of the beam is absorbed by the sample 214; the amount of absorbance being dependent on optical characteristics of the sample 214. As described above, the empty hole 211 or beam dump blocks none of the radiation when the hole 211 is in the beam path, thus generating a residual noise signal. If the transmittance and reflectance of the sample are measured, especially at near normal incidence, then losses, such as the absorbance in the sample, can be easily calculated.

In a third example (not shown), the plate 210 is in a third position of rotation, the reflector region 213 is at the monitoring spot, and the beam impinges on the reflectance standard 216 of the reflectance region 213 at the monitoring spot to generate a reflected reference signal Rs. In addition, when the plate 210 is not in one of the abovementioned first, second, or third positions of rotation, the opaque surface of the plate 210 may be at the monitoring spot, such that the beam is blocked by the opaque plate 210. Under this condition, the dark signal Td may be generated. In sum, during each rotation of the plate 210, each of the opening 211, sample 214, reflectance standard 216 of the reflector region 213, and the surface of the plate 210, can receive the beam at the monitoring spot. In another embodiment, the motor 220 can articulate at least the opening 211, the sample 214 of the sample region 212, and the reflectance standard 216 of the reflector region 213 into the beam.

In addition, the beam may impinge on an angled surface spot 215 of the plate 210. The angled surface spot 215 may be used as a beam-dump to achieve a 0% reference for the reflectance measurement. A surface spot signal R0 may be used in calculating a final reflected signal R, as described below.

In one embodiment, a single source 230 or multiple sources 230, 231 may generate corresponding multiple beams of continuous electromagnetic radiation to generate the signals processed in accordance with the invention. For example, first source 230 can generate a first beam EMR1 that passes through the opening 211 and the sample 214 to create the reference transmittance signal T100 and the sample transmittance signal Ts, respectively, and reflects from the sample 214 and the reflectance standard 216 to generate the sample reflectance signal Rs, and the reference reflectance signal Rr, respectively. Alternatively, a second source 231 may generate a second beam EMR2 that reflects from the sample 214 and the reflectance standard 216 of the reflector region 213 to create the sample reflectance signal Rs and reflected reference signal Rr. The reference reflectance signal Rr is not used for in-situ coating systems, but may be applied to other applications.

In addition, for non-normal or angled measurements, a signal Tstd (not shown) is a transmitted signal through a reference transmittance standard such as a double-polished and parallel glass window. In one embodiment, the transmitted signal Tstd may not be used in in-situ processing and coating applications. The transmitted signal Tstd is useful for compensating for beam walk that may occur in angled transmitted measurements. It is more advantageous to minimize beam walk by keeping the sample 214 thin.

The detection unit 241 may receive signals of the light beam or beams from the various elements of the system, including the opening 211, the sample 214, and the reflector region 213. In one embodiment, a single detection unit, for example, first detection unit 241, may receive both transmittance and reflectance signals of either the beam or multiple beams. In another embodiment, multiple detection units may receive the respective signals of the beam or beams from the various elements of the system.

In addition, the detection unit 241 may generate the dark signal Td. The dark signal Td can be generated whenever the opaque plate 110 blocks the light beam from the detection unit 241. The dark signal Td may be approximately zero when the plate 210 is an opaque plate.

FIG. 2 contains a schematic block diagram of another embodiment of the invention for generating both transmittance and reflectance measurements at various angles of incidence. In FIG. 2, the reflective device 260 receives transmittance signals, for example, reference transmittance signal T100 and sample transmittance signal Ts, and directs the transmittance signals to the first detection unit 241 attached to the monochromator 243. However, in other embodiments, the first detection unit 241 may directly receive transmittance signals of the light beam or beams, without the need for a mirror and monochromator.

The data acquisition and processing apparatus 250 is coupled to the monochromator 243 for processing the transmittance and reflectance signals of the beam or multiple beams. The data acquisition and processing apparatus 250 is also coupled to the first detection unit 241 for processing the transmittance signals of the beam from the opening 211 and the sample 214. In one embodiment, the data acquisition and processing apparatus 250 comprises an analog-to-digital converter (not shown) which converts the received signals into digital data, which are then processed by the data acquisition and processing apparatus 250. The analog-to-digital converter may continuously, and in real-time, sample and convert the analog signals into digital data. The data acquisition and processing apparatus 250 may be a computer, and may further include a data and control interface card (not shown). In this manner, the computer 250 may provide additional functions such as process control, data collection, data processing display, and interface programs.

The data acquisition and processing apparatus 250 generates a calculated final transmitted signal T from the received reference transmittance signal T100, sample transmittance signal Ts, and dark signal Td. In addition, the acquisition and processing apparatus 250 generates the calculated final reflected signal R from the received sample reflectance signal Rs, reflected reference signal Rr, and surface spot signal R0.

As described above, for a normal angle of incidence, the processor generates the transmitted signal T based on the following equation (1):

$$T=[(Ts-Td)/(T100-Td)] \quad (1)$$

In addition, in FIG. 2, for a normal angle of incidence, the processor generates the reflected signal R based on the following equation (2):

$$R=[(Rs-R0)/(R100-R0)] \quad (2)$$

R100 is the true 100% reflectance if the reflectance standard 216 was a perfect reflector. In practice, R100=Rr*Rf, where Rf is a wavelength and angle dependent factor. For example, if, at the measured angle and wavelength, the reflectance standard Rr (a measured parameter) has a known reflectance of 0.8, then Rf would be about 1.2 and R100 is calculated as R100=Rr*1.2. In practice, beam polarization effects are accounted for. Values for Rr are generally known and published to a high degree of accuracy for most polished optical substrates.

As described above, the surface spot signal R0 is an angled surface spot used as a beam dump to achieve a true 0% reference for the reflective measurement. The surface spot signal R0 is subtracted from the sample reflectance signal Rs and the calculated reflected reference signal R100. In this manner, a more accurate measurement of optical thickness of a coating on an optical component can be determined.

In equations (1) and (2), the final transmitted signal T and reflected signal R are calculated based on a normal angle of incidence. However; for non-normal incidence cases, variations on equations (1) and (2) are applied. Such variations would be readily known in the field of the invention. The non-normal incidence case is more complex but is readily computed. Also, calculations for the non-normal incidence case can be generated from these equations using commercial software packages, for example, software packages developed and sold by thin film computation companies. For small deviations from normal, e.g., under 15 degrees, the effects are generally minimal. For larger angles of incidence, one may need to account for spectral shifts, beam walk, and polarization effects on the light beam incident on the sample. At large angles of incidence, e.g., over 25 degrees, the most serious effect can be polarization of the transmitted and reflected components of the beam. By using a polarizing filter in the light path after the light source and before the sample, the salient advantages of the invention can be conserved.

The beam-walk effects can be minimized by using larger aperture optical systems, using thin samples, and/or by orienting the deflection with the long direction of the entrance slits of the monochromator and by using a larger active area detector.

In addition, losses can be determined from the abovementioned final transmitted signal T and reflected signal R. In particular, the processor generates the calculated losses L based on the following equation (3):

$$L=1-T-R \quad (3)$$

In this manner, losses such as absorbance can be determined.

The calculations for calculating the above effects can be found in any standard book on optics such as *Thin-Film Optical Filters*, by Angus Macleod, and *Optics* by Eugene Hecht. Standard software programs that automatically compute such effects are also readily available from TFCalc by Tony Noe of Optical Spectra, Essential Macleod by Angus Macleod and FilmStar by Fred Goldstein. In addition, spectrophotometer manufacturers such as Varian Instruments, Inc., Hitachi and Perkin Elmer, Inc. also provide software that might process the data generated by the present invention.

Referring to FIGS. 2 and 3, the processor may further generate a correct percent reflectance % R based on the following equation:

% $R = 100\% * (Rs/R100)$

As described above, R100 is the true 100% reflectance if the reflectance standard 216 was a perfect reflector, and Rs is the reflectance sample signal. In this equation, polarization effects are ignored. The calculation result % R is a corrected reflectance percentage of the sample 214.

Figure 4:
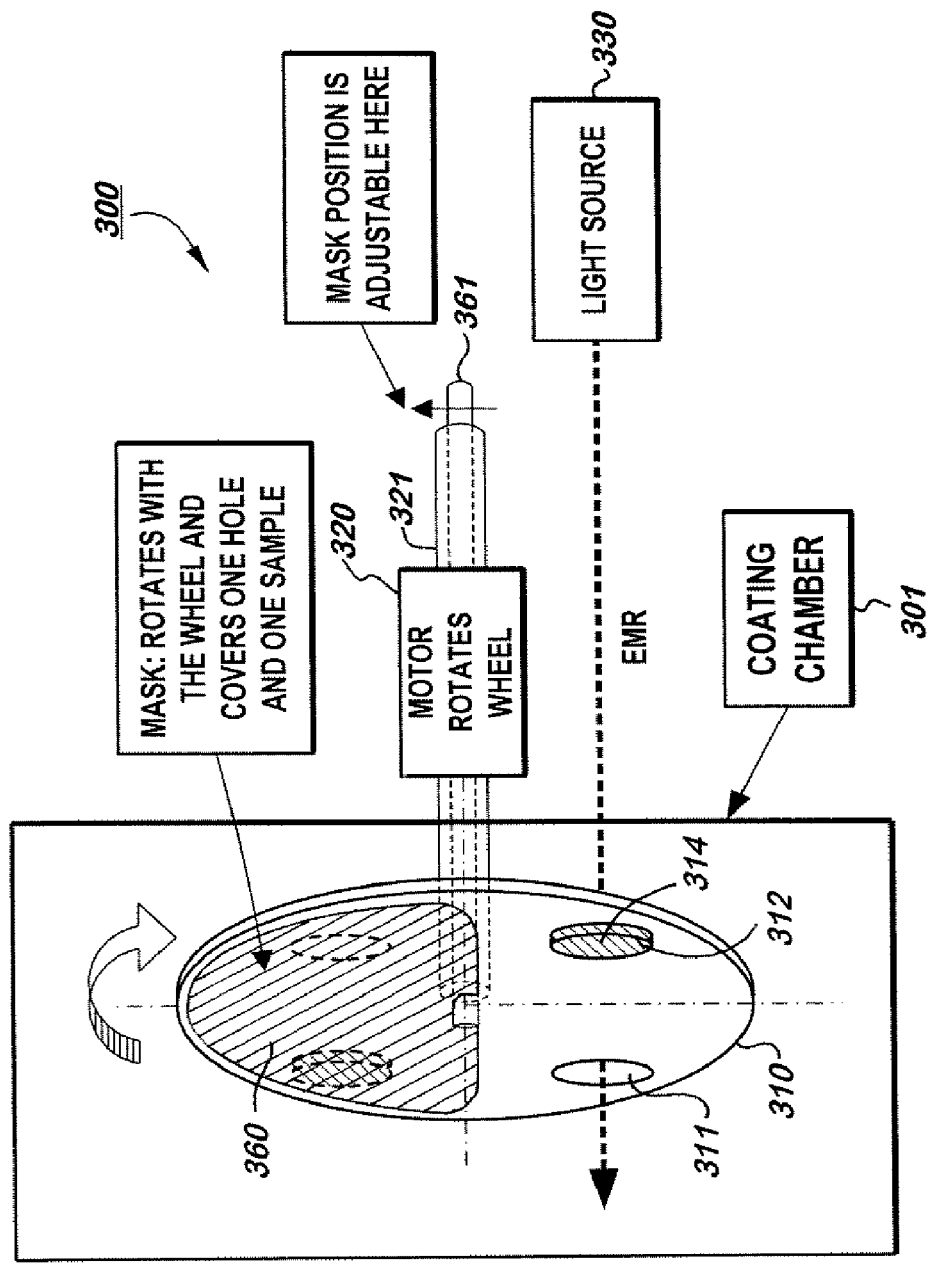
FIG. 4 contains a schematic block diagram of a self-referencing instrument comprising a mask and a rotating mounting member according to another embodiment of the present invention.

FIG. 4 contains a schematic block diagram of an monitoring system 300 employing a mask 360 according to another embodiment of the present invention. In this embodiment, a mounting member 310 in the form of a rotating plate or wheel comprises a plurality of openings and a corresponding plurality of samples coupled to corresponding sample regions. The mask 360 is adjacent to the plate 310, wherein the mask 360 is aligned to expose a single opening 311 and a corresponding single sample 314 to a beam of optical radiation generated by a light source 330 while covering the other openings and corresponding sample regions.

A motor 320 rotates the plate 310 via a hollow shaft 321 that is coupled to the motor 320 and to the center of the wheel or plate 310 for rotating the plate 310. The mask 360 is rotatable with respect to the plate 310 via a second shaft 361 coupled to the mask 360. The mask position is adjustable from the second shaft 361. The first shaft 321 and the second shaft 361 are coaxial. In one embodiment, the plate 310 articulates the opening 311 and corresponding sample 314 into the beam. Other openings and samples in the plate 310 remain masked or otherwise protected from the stream of coating material and reserved for later use in the coating process, for example, in the coating chamber 301.

A computer is connected to other components of the system, including the motor 320, the source 330, and detection unit. A display is attached to the computer, and can be a processed data output device, for example, a TV screen display that presents raw signal data. It should be noted that elements such as the detectors, computer, display, etc., described in connection with the other embodiments described herein, while note specifically shown in the drawing of FIG. 4, are included in the embodiment.

In one embodiment, the masked holes and samples rotate with the rest of the plate 310. By using a hollow rotating shaft or tube, with a coaxial rotating shaft attached to the mask in front of the plate at one end and with a knob with detents at the other end, one can stop the rotation between coating layers and index the mask to a new position before continuing with the next coating layer. After indexing the mask 360, the coating process with the optical process monitoring of the invention continues on the newly exposed sample and opening.

This feature is advantageous in the case of transmittance monitoring of a coating deposition process where the first coating layer is metallic, for example, aluminum or gold, and the exposed sample becomes opaque to monitoring light, thus making it ineffective for monitoring further coating deposition.

Figure 5:
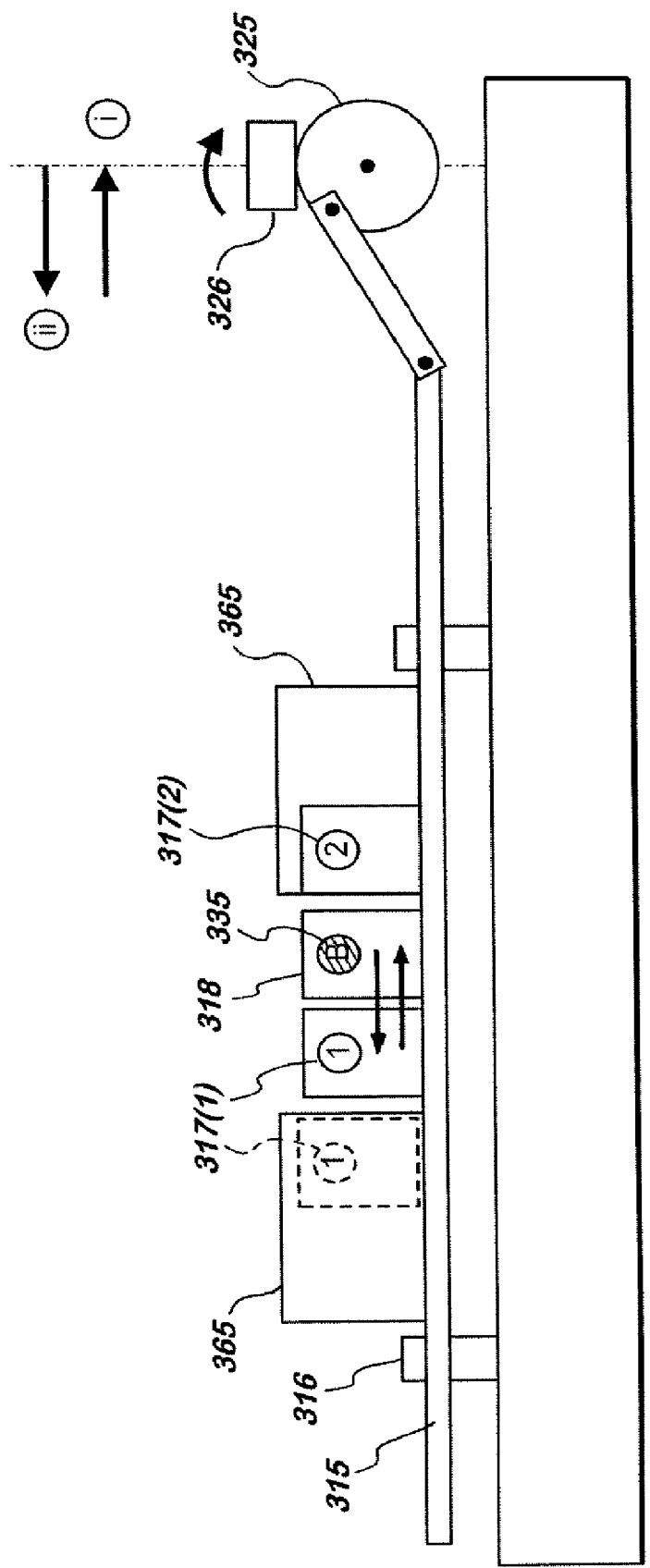
FIG. 5 contains an illustrative view of a self-referencing instrument of FIG. 4 further comprising a mask and a mounting member as a shaft according to another embodiment of the invention.

FIG. 5 contains an illustrative view of a self-referencing instrument of FIG. 4 further comprising a mask and a mounting member as a shaft according to another embodiment of the invention. FIG. 5 does not require rotating plates but may be considered to be less advantageous than the rotating embodiments. In this embodiment, the mounting member 315 supports at least one opening 318, a first witness sample 317(1) or chip number 1 and a second witness sample 317(2). The opening 318 can be between samples 317(1), 317(2). Alternatively, a reference cell comprising the opening 318 can be coupled to the shaft 315. In all embodiments, the apertures or openings of witness samples 317(1), 317(2), and the reference cell are identical. Linear shaft bearings 316 permit the shaft 315 to move along an axis such that the witness samples and openings can be positioned in the path of the electromagnetic radiation. The cam assembly 325 can translate the shaft in and out of the light path B for changing the exposed sample. During coating operation, the cam assembly 325 is in position (i) wherein the cam assembly 325 articulates the first witness sample 317(1) and the opening 318 in and out of a light path B of the light beam 335, while samples 317(2) remain masked by the mask 365. Light beam 335 is a stationary collimated beam, similar to FIG. 1, in a beam aperture position. When witness sample 317(2) is to be coated, the cam assembly 325 and attached motor 326 is articulated to position (ii). The motor 326 and cam assembly 325 articulate the opening (not shown) and witness sample 317(2) in and out of the radiation while witness sample 317(1) remains masked by the mask 365. That is, witness sample 317(1) is masked when witness sample 317(2) is in use.

Figure 6:
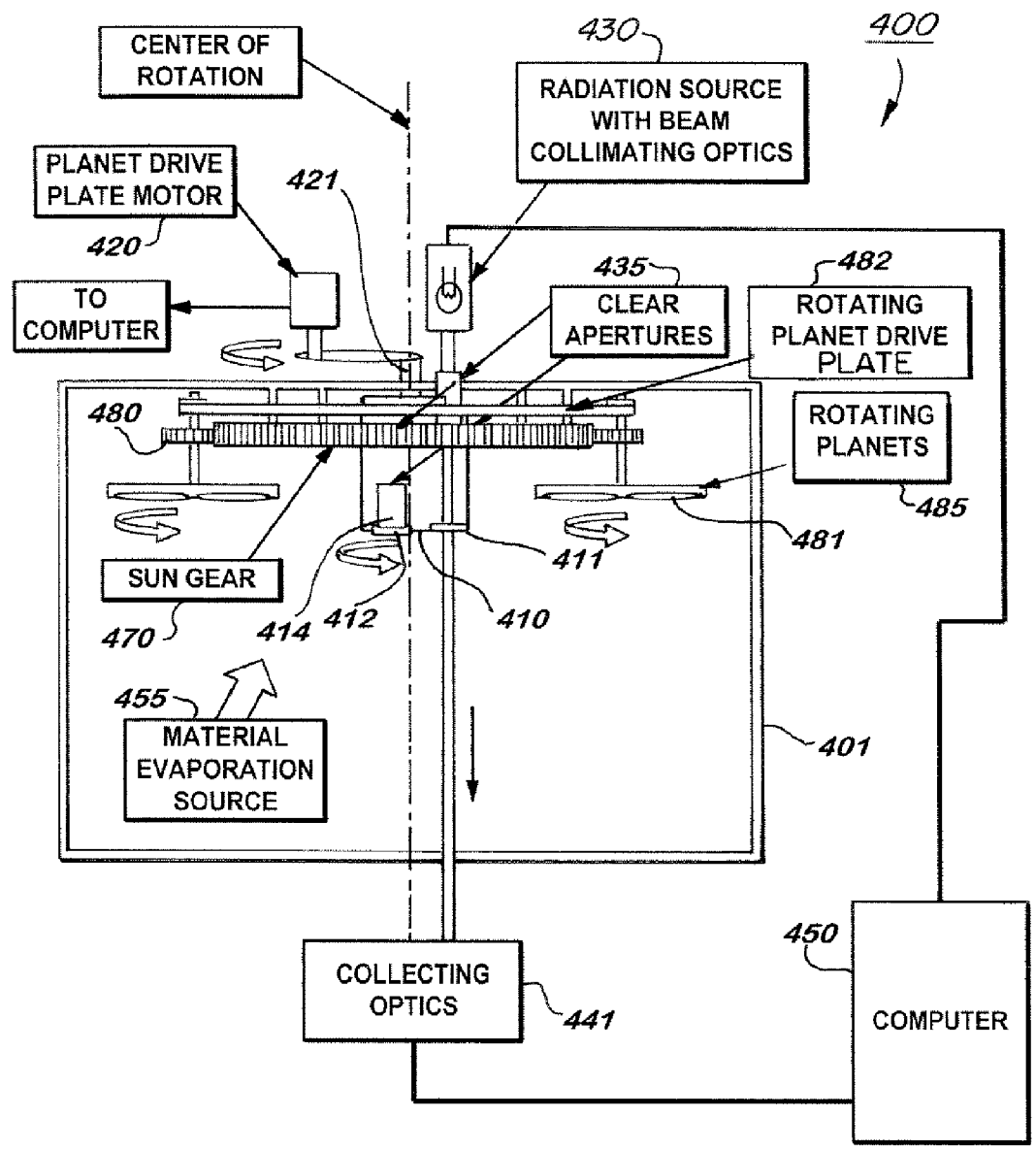
FIG. 6 contains an illustrative view of a planetary coating system according to another embodiment of the present invention.

In addition, a computer is connected to other components of the system, including the motor 326, the source of beam, and a detection unit. A display is attached to the computer, and can be a processed data output device, for example, a TV screen display that presents raw signal data. It should be noted that elements such as the detectors, computer, display, etc., described in connection with the other embodiments described herein, while note specifically shown in the drawing of FIG. 5, are included in the embodiment. FIG. 6 contains an illustrative front view of a planetary coating system 400 according to another embodiment of the present invention which uses the monitoring system of the invention described herein to monitor a coating process. The coating system 400 comprises a stationary sun gear 470, a rotating planet drive plate 482, and a plurality of rotating planetary gears 480 attached to the perimeter of the drive plate 482, and meshed to the perimeter of the stationary sun gear 470. Each planetary gear 480 is coupled to rotating planets 485 containing components or production substrates 481. The rotating planets are also referred to as planetary stations. In addition, the coating system 400 comprises a rotatable mounting member or plate 410.

The mounting member 410 comprises at least one opening 411 and at least one sample region 412 containing a sample 414 that is coupled to the mounting member 410. The opening 411 and sample region 412 are substantially equidistant from the center of the mounting member 410. Further, the sample 414 may be polished on both sides, such that both sides of the sample 414 are substantially parallel and flat. The sample is constructed so as to offer a minimum of deflection, scatter, displacement, divergence, convergence or distortion to the impinging beam of electromagnetic radiation.

A sun planetary motor drive 420 for planetary motion rotates or articulates the mounting member 410 via a shaft 421 that is coupled to the motor drive 420 at a large hole in the center of the sun gear 470. The mounting member 410 comprising the sample 414 and the aperture or opening 411 is attached to, and rotates with, the planet drive plate 482. The mounting member 410 can be rotated by the motor drive 420 at various speeds, and, in one particular embodiment, at speeds ranging at least from 5 to about 20 RPM.

A source 430 generates a beam at the mounting member 410 through clear openings or clear apertures 435. The source 430 can be a source of electromagnetic radiation, such as a radiation source with beam collimating optics.

In one embodiment, the planetary coating system 400 further comprises a mask (not shown), as described in connection with FIG. 6, adjacent to the mounting member 410, wherein the mask permits a single sample region 412 and corresponding opening 411 of a plurality of openings and sample regions to be exposed to the coating process and the beam for monitoring the single sample. In this manner, the mask permits any remaining samples of the mounting member 410 to be placed in reserve until the currently exposed sample is no longer used for monitoring. That is, the embodiment of FIG. 4 can apply to this planetary optical monitoring embodiment.

Collecting optics/detector 441 receives transmittance signals of the light beam from the opening 411 and the sample 414. In addition, the collecting optics/detector 441 may generate a dark signal Td. The dark signal Td can be generated whenever the mounting member 410 blocks the light beam from the collecting optics/detector 441. The dark signal Td may be approximately zero when the mounting member 410 is an opaque plate.

A data acquisition and processing apparatus, i.e. computer, 450 in accordance with the foregoing description is coupled to the collecting optics/detector 441 for processing the signals of the beam from the opening 411 and sample. The data acquisition and processing apparatus may comprise an analog-to-digital converter to convert the received signals into digital-data, which are then processed by the data acquisition and processing apparatus. The data acquisition and processing apparatus may be a computer, and may further include a data and control interface card. In this manner, the computer may provide additional functions such as process control, data collection, data processing display, and interface programs. The computer 450 is connected to other components of the system, including the motor 420, the source 430, and collecting optics 441. A display can be a processed data output device, for example, a TV screen display that presents raw signal data.

During a coating operation, the planetary gears 480 and the mounting member 410 rotate while the substrates or components 481 and the sample are coated with at least one layer of a coating material. A coating subsystem comprising a material evaporation source 455 may be used to deposit the coating material on the components 481 and the sample inside the chamber 401. The coating subsystem may be a conventional coating subsystem. The chamber 401 can be a conventional coating chamber, such as a vacuum coating chamber.

In a preferred embodiment, the rotating mounting member 410 is lower than the rotating planetary gears 480 holding the components 481 in the coating chamber 401. In this manner, during a deposition of a layer of coating material, the coating layer applied to the sample 414 has a greater thickness than the corresponding coating layer applied to the components 481. This may result in an improved monitor-to-work ratio, also referred to as a tooling factor, which may in turn provide improved accuracy of the control rate during the coating material deposition process.

This feature of the present invention as illustrated in FIG. 6 is advantageous over conventional systems in that by replacing the stationary monitoring glass of conventional coating systems with a continuously rotating disk containing at least one opening and one sampling glass, the benefits described above may be achieved.

Figure 7:
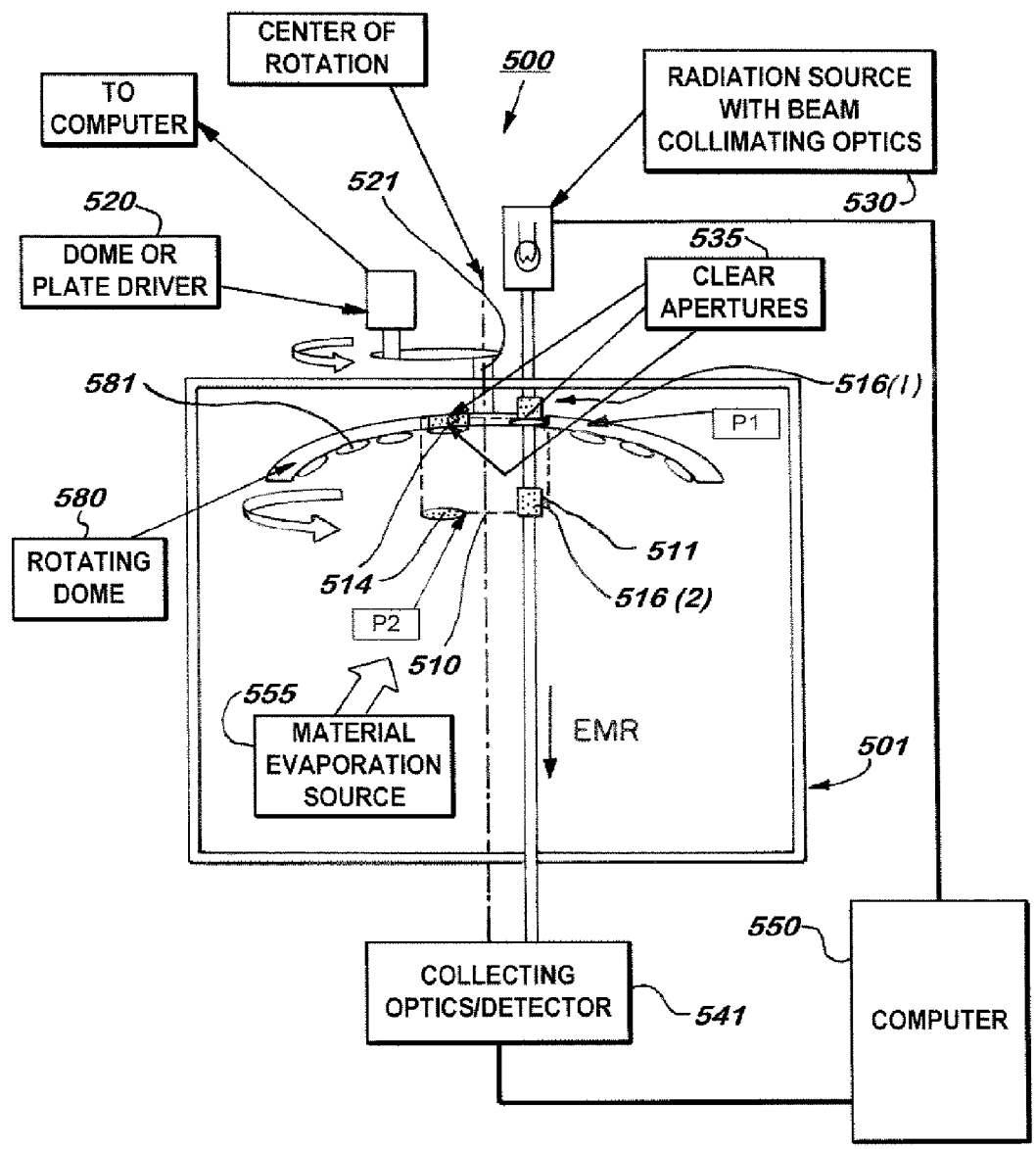
FIG. 7 contains an illustrative view of a coating system comprising a dome according to another embodiment of the present invention.

FIG. 7 contains an illustrative view of a coating system 500 comprising a rotating dome 580 according to another embodiment of the present invention which uses the monitoring system of the invention described herein to monitor a coating process. In one embodiment, for example, at position PI, the witness sample 514 is on the dome with production substrates being coated and monitored, whereby the sample 514 and the empty aperture 511 rotates with the dome 580 or plate containing production substrates, and at the apex of the dome in and out of the beam of electromagnetic radiation (EMR), such as a light beam, and all the production substrates 581 are coated along with the monitoring sample 514. The beam of electromagnetic radiation passes through a hollow tube 516(1) at position P1. In another alternative embodiment, for example, in position P2, a mounting member 510 is positioned lower than the dome 580. The mounting member comprises at least one opening 511 and at least one sample region 514 containing a sample that is coupled to the dome. It is preferable that the least one opening 511 and at least one sample region 514 are substantially equidistant from the center of the mounting member 510. The beam of electromagnetic radation passes through a hollow tube 516(2) at position P2.

Further, the sample may be polished on both sides, such that both sides of the sample are substantially parallel and flat. The sample is constructed so as to offer a minimum of deflection, scatter, displacement, divergence, convergence or distortion to the impinging beam of electromagnetic radiation.

A motor, or dome or plate driver 520, located above the chamber 401, rotates the dome and the mounting member 510. The driver 520 rotates the dome 580 via a shaft 521 that is coupled to the driver 520 at a center of rotation.

A source 530 generates a continuous beam at the mounting member 510 through an optically transparent port window in the chamber 501. The source 530 can be a source of optical radiation, such as a light source.

A data acquisition and processing apparatus, i.e. computer, 550 in accordance with the foregoing description is coupled to the collecting optics/detector 541 for processing the signals of the beam from the opening 411 and sample. The data acquisition and processing apparatus may comprise an analog-to-digital converter to convert the received signals into digital data, which are then processed by the data acquisition and processing apparatus. The data acquisition and processing apparatus may be a computer, and may further include a data and control interface card. The computer 550 is connected to other components of the system, including the motor 520, the source 530, and collecting optics 541. A display can be a processed data output device, for example, a TV screen display that presents raw signal data.

In one embodiment, the coating system 500 further comprises a mask (not shown) adjacent to the mounting member 510, wherein the mask permits a single sample region 512 and corresponding opening 511 of a plurality of openings and sample regions to be exposed to the coating process and the beam for monitoring the single sample. In this manner, the mask permits any remaining samples of the mounting member 510 to be placed in reserve until the currently exposed sample is no longer used for monitoring.

In accordance with the invention in the coating system of FIG. 7, the components 581 and the sample 514 are coated inside the chamber 501 with at least one layer of a coating material during a coating operation. This may be achieved by a coating subsystem comprising a material evaporation source 555 supporting coating material advancing. In position P2, as described above, the rotating mounting member 510 is lower than the dome 580 holding the components 581.

In this manner, during a coating layer deposition process, a coating layer applied to the sample has a greater thickness than the corresponding coating layer applied to the components 581, which improves the accuracy of the control rate of the coating material deposition. The chamber 501 can be a conventional coating chamber such as a vacuum coating chamber.

Figure 8:
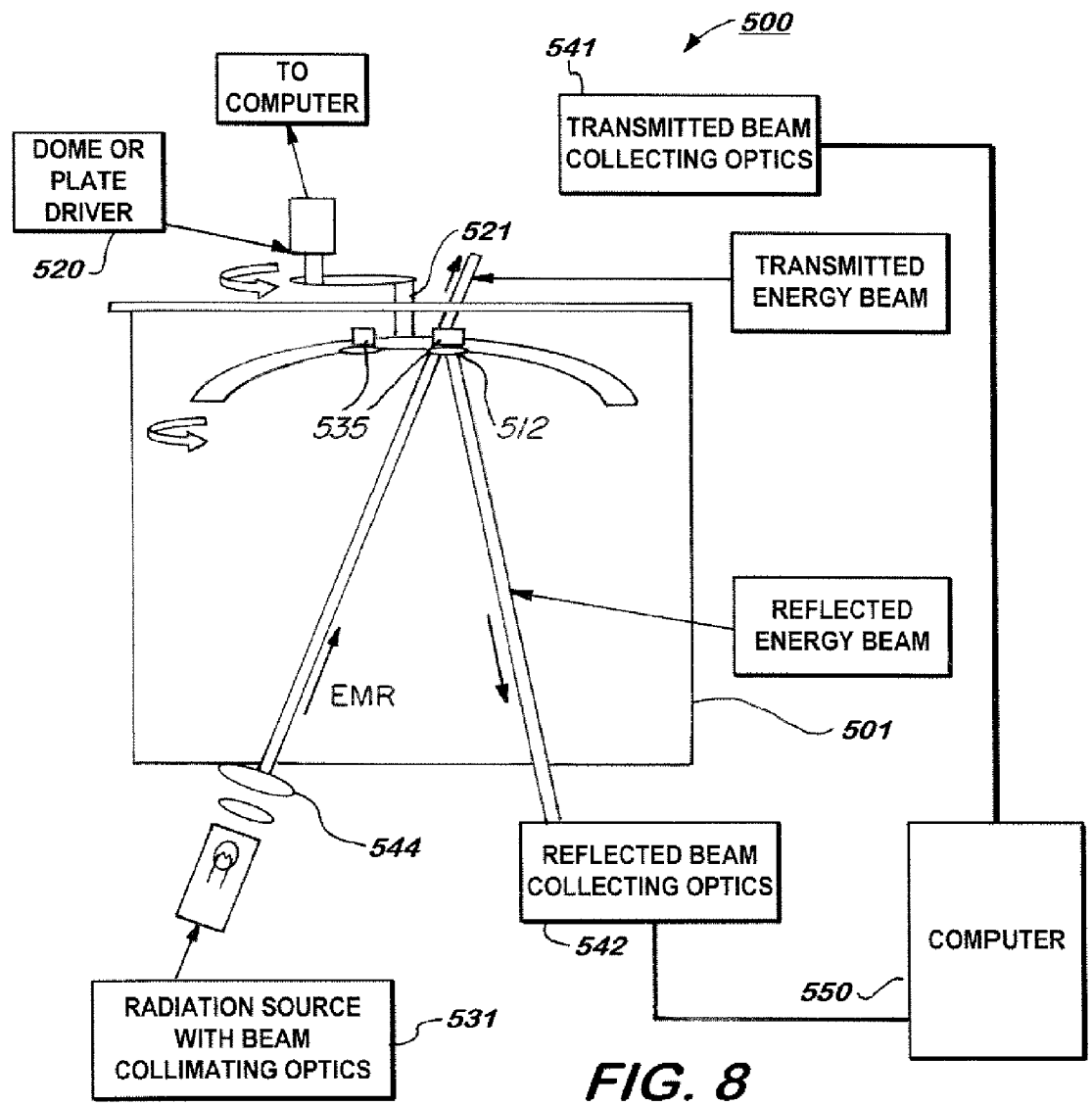
FIG. 8 contains an illustrative view of the system of FIG. 7 expanded for simultaneously monitoring reflectance and transmittance in a coating operation, according to another embodiment of the present invention.

FIG. 8 contains an illustrative view of the coating system of FIG. 7 for measuring a reflectance signal as well as a transmitted signal according to another embodiment of the present invention. In FIG. 8, a source 531 generates a beam of electromagnetic radiation. The source 531 may be a radiation source with beam collimating optics. In FIG. 8, the radiation partially passes through the sample 514 to create a transmitted energy beam, or sample transmittance signal, and partially reflects from the sample 514 to generate a reflected energy beam, or sample reflectance signal. The sample transmittance and reflectance signals are received by optical assemblies 541, 542, respectfully referred to in FIG. 8 as beam collecting optics. The transmitted beam collecting optics 541 and the reflected beam collecting optics 542 may be coupled to optical fiber. The data acquisition and processing apparatus 550 is coupled to the transmitted beam collecting optics 541 and reflected beam collecting optics 542, respectfully, for processing the signals of the beam from sample 514. In addition, a beam polarizer 544 is located along the beam path just before the beam enters the chamber 501.

As described above, the self-referencing instrument of the present invention corrects for various sources of noise. In contrast, most conventional optical monitors incompletely adjust for drifting signals. Conventional chopped or pulsed energy sources do not stop signal drift and furthermore they can contribute to the optical and/or electrical noise and thereby degrade the signal they are supposed to improve. Also, the external chopper or pulsed light source generally requires additional components in order to work adequately. In particular, they need both a source and detector to generate a chopped reference signal and a lock-in amplifier, which often introduces additional noise to the signal. Light choppers and pulsed light sources generally add optical and electrical noise to the signal. Also, these additional components provide added capital and operating costs to the photometer. Also, these additional components provide added complexity to the photometer, which can reduce the reliability of the system.

Another advantage of the present invention over the combination of a light chopper and lock-in amplifier is that, with the conventional light chopper, the signal is not chopped in the ideal location which is the same spot where the substrate being coated and monitored. For example, as the beam-directing lenses, windows, and mirrors between the chopper and substrate become coated or creep, these effects can add un-compensatable noise or drift to the signal. In contrast, the present invention is mostly immune to such sources of signal drift. Even sudden steps up or down in the signal are ratioed out with this invention as soon as the next complete dome revolution occurs.

In addition, conventional optical monitoring systems are incapable of producing a high fidelity spectral scan of the in-situ production components. The present invention, on the other hand, in combination with a modern automated monochromator and high-speed data collecting components, for example, computer and data acquisition/digitizing cards, facilitates accurate spectral scans of the sample in situ.

Obtaining an accurate spectral scan at various points in the coating process could be a useful research or troubleshooting tool. For example, one might wish to know the spectral properties of a coating after the coating run and before cool down or venting the chamber.

Figure 9:
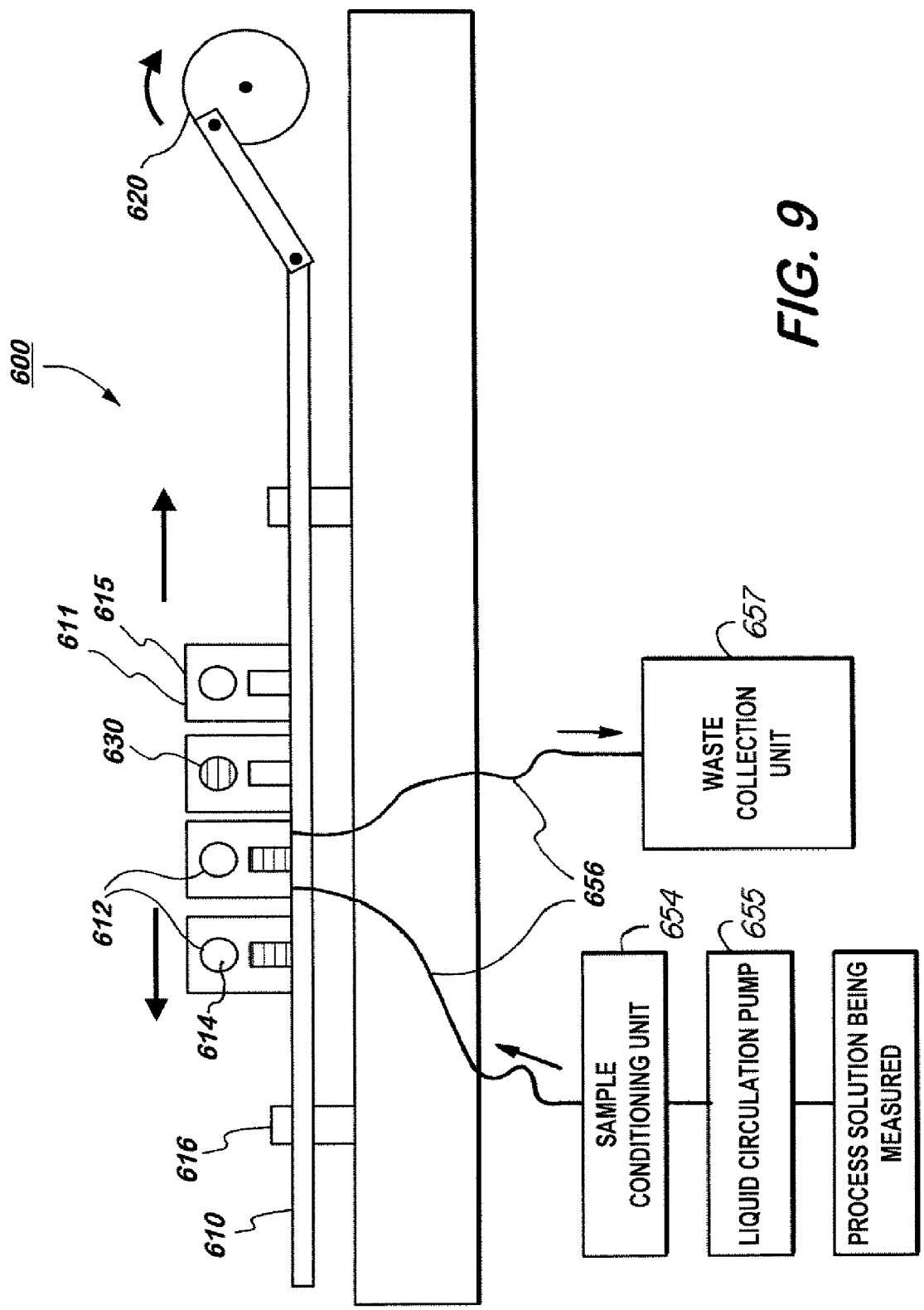
FIG. 9 contains an illustrative front view of a liquid flow-cell spectrophotometer according to another embodiment of the present invention.

FIG. 9 contains an illustrative view of a flow cell spectrophotometer according to another embodiment of the present invention which used the monitoring approach of the invention. The spectrophotometer 600 comprises a mounting member in the form of a shaft 610, a liquid cell circulation system, a driver 620, a directed beam 630, a detection unit (not shown), and a processor (not shown). It should be noted that the direction of the beam 630 from source to detector is out of the page. The mounting member 610 includes at least one reference cell 615 comprising an opening 611, and at least one sample cell 612 comprising a sample 614, which are mounted to the shaft 610. Linear shaft bearings 616 permit the shaft 610 to move along an axis such that the sample and opening can be positioned in the path of the electromagnetic radiation 630. The sample cell 612 receives a process fluid to be measured. The fluid circulation system provides the process fluid to the sample cells 612. The fluid can be a liquid or a gas.

The fluid circulation system further comprises a fluid circulation pump 655, a sample conditioning unit 654, a waste collection unit 657, and flexible tubing 656 for delivering the process solution being measured to the sample cells.

During operation, the driver, or the motor-driven wheel and cam assembly 620, articulates the sample cell 612 and reference cell 615 in and out of a beam of electromagnetic radiation 630. It is preferable that the aperture of each sample cell 612 be identical to the aperture of the reference cell 615 The beam can be a stationary collimated beam, in a beam aperture position, for example, as described in FIG. 1.

When the opening 611 is articulated into the beam, the shaft 610 is in a first position along the axis, and the opening 611 receives the beam 630, whereby the detection unit (not shown) receives the beam that has passed through the opening 611 to create a reference signal. When a sample cell 612 is articulated into the beam, the shaft 610 is in a second position along the axis, and the sample cell 612 containing the liquid or gas being analyzed receives the beam that passes through the process fluid in the sample cell 612, thereby creating sample signals in a similar manner as described above. In one embodiment, transmittance and reflectance signals are generated in a similar manner as described above. In this manner, at least one detection unit receives the reference signal and the sample signal, and a processor processes the reference signal and the sample signal, in a similar manner as described above. The processor is connected to other components of the system, including the motor 620, the source 630, and a defector. A display can connected to the computer as a processed data output device, for example, a TV screen display that presents raw signal data. It should be noted that elements such as the detectors, computer, display, etc., described in connection with the other embodiments described herein, while note specifically shown in the drawing of FIG. 9, are included in the embodiment.

This feature of the present invention as illustrated in FIG. 9 is advantageous in that by preparing substrates that one wishes to monitor, for example, a certain protein in a fluid or mercury compounds going up a smoke-stack, the invention can be implemented with flow cells, which is particularly useful in applications such as industrial fluid process monitors.

As described above, the present invention is directed to a self-referencing instrument that creates a reference signal at the same location as, and at approximately the same time as, the sample signal. In particular applications, the invention is applicable to controlling a coating process, monitoring in-situ processes, and measuring sample properties. In particular, the present invention offers enhanced monitoring and control over the coating thickness on optical components to a level of accuracy beyond those currently achieved by conventional monitoring systems. For example, the present invention is particularly useful in providing an apparatus and method for making very complex multi-band filters, broad and deep anti-reflective coatings, and non-quarter-wave narrow bandpass optical filters where small coating errors can cause failure to meet the specifications.

The present invention continuously corrects for most common sources of error and is especially strong at canceling optical drift since the signal is corrected for such errors with every revolution of the substrate. The present invention continuously corrects for most common sources of error because the errors seen at the sample are also seen by the reference at the same place, and immediately ratioed out. By combining the present invention with suitable turning-point algorithms, and/or the use of frequency modulation schemes, and/or the use of simultaneous two-wavelength monitoring, and/or the integration of the signal from a deposition-rate monitor such as an oscillating crystal, this technique dramatically improves the accuracy of traditional turning-point monitoring methods.

In all embodiments herein, the apertures of the at least one sample and the at least one opening are substantially the same.

Another feature of the present invention is that, by using an appropriate high intensity energy source, such as a laser, and by blocking the coating to the sample during most of its revolution the present invention can be used in monitoring and controlling filters with high optical densities, and thereby the thickness of nearly opaque materials such as metals, paints, and non-specular coatings that mainly scatter or absorb energy over wide spectral ranges. This feature is particularly useful in precision thin plating and opaque coating applications.

The present invention may also apply to large area coating systems, whereby in order to update and average the signal and reference more accurately when monitoring at large radii in a large plate, additional monitored samples or substrates and openings can be included.

Another feature of the present invention is that a high-precision transmitted and reflected energy spectrophotometer with a rotating sample holder plate, that also includes a required empty reference hole, i.e., an opening, and reference transmittance and/or reflectance standards, can be applied to a simple, rugged, low-cost spectrophotometer.

It should be noted that when the beam of electromagnetic radiation impinges on the sample, various photo-reactive phenomena can occur. These phenomena include fluorescence, heating, darkening, re-radiation, non-linear optics, Raman effects, and other such phenomena. The present invention is applicable to processing such phenomena.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A self-referencing instrument for measuring properties of electromagnetic radiation, comprising:
   a source of the electromagnetic radiation;
   a mounting member to which a sample can be coupled, the mounting member moving the sample such that, in a first position, the electromagnetic radiation impinges on the sample, and, in a second position, the electromagnetic radiation passes through an opening of the mounting member, such that the electromagnetic radiation does not impinge on the sample;
   a detection unit for receiving the electromagnetic radiation and generating signals therefrom, the detection unit receiving the electromagnetic radiation from the sample and generating a sample signal when the sample is in the first position, and the detection unit receiving the electromagnetic radiation from the source and generating a reference signal when the sample is in the second position; and
   a processor coupled to the detection unit for processing the reference signal and the sample signal;
   wherein the mounting member can move the sample between the first and second positions such that multiple reference signals can be generated to correspond with multiple sample signals;
   wherein, when the sample is in the first position, the electromagnetic radiation received by the detection unit is transmitted through the sample; and
   wherein, when the sample is in the first position, the electromagnetic radiation received by the detection unit is reflected from the sample.

2. The instrument of claim 1, wherein the mounting member is rotatable, and wherein the sample and the opening are rotated into the beam of electromagnetic radiation.

3. The instrument of claim 1, wherein the mounting member articulates the sample and the opening into the beam of electromagnetic radiation.

4. The instrument of claim 1, wherein, when the sample is in a third position, the electromagnetic radiation is substantially blocked from the detection unit.

5. The instrument of claim 1, wherein the instrument is a photometer.

6. The instrument of claim 1, wherein the instrument is a spectrophotometer.

7. The instrument of claim 1, wherein the mounting member is a substantially circular plate.

8. The instrument of claim 1, wherein the mounting member is a shaft movable along an axis, the sample being coupled to the shaft.

9. The instrument of claim 1, the processor computes losses from the processed sample signal and reference signal.

10. The instrument of claim 1, wherein a speed of movement of the mounting member is optimized for measuring the properties of the electromagnetic radiation.

11. The instrument of claim 1, wherein apertures for the sample and the opening are substantially the same.

12. The instrument of claim 1, wherein the sample provides a minimum of deflection, scatter, displacement, divergence, convergence, and distortion to the impinging beam of electromagnetic radiation.

13. The instrument of claim 1, wherein the processor processes the reference signal and the sample signal to determine a thickness of a coating being applied to the sample.

14. The instrument of claim 1, further comprising a mask adjacent to the mounting member, wherein the mounting member comprises a plurality of openings and a corresponding plurality of sample regions, the mask exposing a single opening and a corresponding single sample to the radiation while covering other openings and corresponding sample regions.

15. The instrument of claim 14, wherein the driver is coupled to the mounting member by a first shaft, and wherein the mask is rotatable with respect to the mounting member via a second shaft coupled to the mask.

16. The instrument of claim 15, wherein the first and second shafts are coaxial.

17. The instrument of claim 1, wherein the processor processes spectral features of a coating being applied to the sample.

* * * * *